United States Patent
Krivoruchko

(10) Patent No.: US 7,625,403 B2
(45) Date of Patent: Dec. 1, 2009

(54) VALVED CONDUIT DESIGNED FOR SUBSEQUENT CATHETER DELIVERED VALVE THERAPY

(75) Inventor: Mike Krivoruchko, Forestville, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 502 days.

(21) Appl. No.: 11/278,646

(22) Filed: Apr. 4, 2006

(65) Prior Publication Data

US 2007/0233237 A1    Oct. 4, 2007

(51) Int. Cl.
*A61F 2/24* (2006.01)
(52) U.S. Cl. ............ 623/2.17; 623/2.11; 623/1.24
(58) Field of Classification Search ........ 623/1.24–2.19
See application file for complete search history.

(56) References Cited

U.S. PATENT DOCUMENTS

| | | |
|---|---|---|
| 3,334,629 A | 8/1967 | Cohn |
| 3,540,431 A | 11/1970 | Mobin-Uddin |
| 3,628,535 A | 12/1971 | Ostrowsky et al. |
| 3,642,004 A | 2/1972 | Osthagen et al. |
| 3,657,744 A | 4/1972 | Esek |
| 3,671,979 A | 6/1972 | Moulopoulos |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,056,854 A | 11/1977 | Boretos et al. |
| 4,106,129 A | 8/1978 | Carpentier et al. |
| 4,233,690 A | 11/1980 | Akins |
| 4,291,420 A | 9/1981 | Reul |
| 4,425,908 A | 1/1984 | Simon |
| 4,501,030 A | 2/1985 | Lane |
| 4,580,568 A | 4/1986 | Gianturco |
| 4,610,688 A | 9/1986 | Silvestrini et al. |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,710,192 A | 12/1987 | Liotta et al. |

(Continued)

FOREIGN PATENT DOCUMENTS

EP          1057459         2/2000

(Continued)

OTHER PUBLICATIONS

P. Bonhoeffer, MD, et al., "Transcatheter Implantation of a Bovine Valve in a Pulmonary Position—A Lamb Study," pp. 8-3-816; Aug. 2000.

(Continued)

*Primary Examiner*—Suzette J Gherbi

(57) ABSTRACT

A system for treating a vascular condition includes a conduit having an inner wall and at least one locking member positioned within the inner wall of the conduit. The system also includes a stented valve positioned in contact with the locking member within the inner wall of the conduit. A method for treating a vascular condition includes inserting a conduit with a stented valve into a target region of a vessel, positioning a contact portion of the stented valve against a locking portion of the conduit and preventing migration of the stented valve within the conduit based on the positioning.

16 Claims, 10 Drawing Sheets

U.S. PATENT DOCUMENTS

| | | |
|---|---|---|
| 4,733,665 A | 3/1988 | Palmaz |
| 4,819,751 A | 4/1989 | Shimada et al. |
| 4,834,755 A | 5/1989 | Silverstrini et al. |
| 4,856,516 A | 8/1989 | Hillstead |
| 4,872,874 A | 10/1989 | Taheri |
| 4,909,252 A | 3/1990 | Goldberger |
| 4,917,102 A | 4/1990 | Miller et al. |
| 4,954,126 A | 9/1990 | Wallsten |
| 4,994,077 A | 2/1991 | Dobben |
| 5,002,559 A | 3/1991 | Tower |
| 5,156,621 A | 10/1992 | Navia et al. |
| 5,161,547 A | 11/1992 | Tower |
| 5,163,953 A | 11/1992 | Vince |
| 5,197,979 A | 3/1993 | Quintero et al. |
| 5,217,483 A | 6/1993 | Tower |
| 5,332,402 A | 7/1994 | Teitelbaum et al. |
| 5,336,258 A | 8/1994 | Quintero et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,431,676 A | 7/1995 | Dubrul et al. |
| 5,507,767 A | 4/1996 | Maeda et al. |
| 5,545,211 A | 8/1996 | An et al. |
| 5,554,185 A | 9/1996 | Block et al. |
| 5,575,818 A | 11/1996 | Pinchuk |
| 5,645,559 A | 7/1997 | Hachtman et al. |
| 5,667,523 A | 9/1997 | Bynon et al. |
| 5,674,277 A | 10/1997 | Freitag |
| 5,695,498 A | 12/1997 | Tower |
| 5,713,953 A | 2/1998 | Vallana et al. |
| 5,800,456 A | 9/1998 | Maeda et al. |
| 5,817,126 A | 10/1998 | Imran |
| 5,824,043 A | 10/1998 | Cottone, Jr. |
| 5,824,053 A | 10/1998 | Khosravi et al. |
| 5,824,056 A | 10/1998 | Rosenberg |
| 5,824,064 A | 10/1998 | Taheri |
| 5,840,081 A | 11/1998 | Andersen et al. |
| 5,855,597 A | 1/1999 | Jayaraman |
| 5,855,601 A | 1/1999 | Bessler et al. |
| 5,860,966 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,907,893 A | 6/1999 | Zadno-Azizi et al. |
| 5,925,063 A * | 7/1999 | Khosravi .................... 606/200 |
| 5,944,738 A | 8/1999 | Amplatz et al. |
| 5,954,766 A | 9/1999 | Zadno-Aziz et al. |
| 5,957,949 A | 9/1999 | Leonhardt et al. |
| 5,984,957 A | 11/1999 | Laptewicz, Jr. et al. |
| 6,001,126 A | 12/1999 | Nguyen-Thien-Nhon |
| 6,027,525 A | 2/2000 | Suh et al. |
| 6,042,598 A | 3/2000 | Tsugita et al. |
| 6,051,014 A | 4/2000 | Jang |
| 6,123,723 A | 9/2000 | Konya et al. |
| 6,146,366 A | 11/2000 | Schachar |
| 6,162,245 A | 12/2000 | Jayaraman |
| 6,168,614 B1 | 1/2001 | Andersen et al. |
| 6,200,336 B1 | 3/2001 | Pavcnik et al. |
| 6,221,006 B1 | 4/2001 | Dubrul et al. |
| 6,221,091 B1 | 4/2001 | Khosravi |
| 6,241,757 B1 | 6/2001 | An et al. |
| 6,254,436 B1 | 7/2001 | Nitta et al. |
| 6,258,114 B1 | 7/2001 | Konya et al. |
| 6,258,115 B1 | 7/2001 | Dubrul et al. |
| 6,258,120 B1 | 7/2001 | McKenzie et al. |
| 6,277,555 B1 | 8/2001 | Duran et al. |
| 6,309,417 B1 | 10/2001 | Spence et al. |
| 6,327,772 B1 | 12/2001 | Zadno-Aziz et al. |
| 6,338,735 B1 | 1/2002 | Stevens |
| 6,342,070 B1 | 1/2002 | Nguyen-Thien-Nhon |
| 6,348,063 B1 | 2/2002 | Yassour et al. |
| 6,350,282 B1 | 2/2002 | Eberhardt |
| 6,352,708 B1 | 3/2002 | Duran et al. |
| 6,364,905 B1 | 4/2002 | Simpson et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,458,153 B1 | 10/2002 | Bailey et al. |
| 6,468,303 B1 | 10/2002 | Amplatz et al. |
| 6,475,239 B1 | 11/2002 | Campbell |
| 6,482,228 B1 | 11/2002 | Norred |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,509,930 B1 | 1/2003 | Hirano et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,558,417 B2 | 5/2003 | Peredo |
| 6,562,058 B2 | 5/2003 | Seguin et al. |
| 6,569,196 B1 | 5/2003 | Vesely |
| 6,592,546 B1 | 7/2003 | Barbut et al. |
| 6,622,604 B1 | 9/2003 | Chouinard et al. |
| 6,632,243 B1 | 10/2003 | Zando-Azizi et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,887,266 B2 | 5/2005 | Williams et al. |
| 6,890,330 B2 | 5/2005 | Streeter et al. |
| 6,896,690 B1 | 5/2005 | Lambrecht et al. |
| 6,929,653 B2 | 8/2005 | Streeter |
| 7,021,314 B1 * | 4/2006 | Lane ...................... 128/207.29 |
| 7,276,084 B2 * | 10/2007 | Yang et al. .................. 623/2.14 |
| 2001/0007956 A1 | 7/2001 | Letac et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2002/0032480 A1 | 3/2002 | Spence et al. |
| 2002/0032481 A1 | 3/2002 | Gabbay |
| 2002/0052651 A1 | 5/2002 | Myers et al. |
| 2002/0058995 A1 | 5/2002 | Stevens |
| 2002/0077696 A1 | 6/2002 | Zadno-Azizi et al. |
| 2002/0095209 A1 | 7/2002 | Zadno-Azizi et al. |
| 2002/0111674 A1 | 8/2002 | Chouinard et al. |
| 2002/0151970 A1 | 10/2002 | Garrison et al. |
| 2002/0161392 A1 | 10/2002 | Dubrul |

| | | | |
|---|---|---|---|
| 2002/0161394 A1 | 10/2002 | Macoviak et al. | |
| 2002/0193871 A1 | 12/2002 | Beyersdorf et al. | |
| 2003/0014104 A1 | 1/2003 | Cribier | |
| 2003/0023303 A1 | 1/2003 | Palmaz et al. | |
| 2003/0028247 A1 | 2/2003 | Cali | |
| 2003/0036791 A1 | 2/2003 | Philipp et al. | |
| 2003/0040771 A1 | 2/2003 | Hyodoh et al. | |
| 2003/0040772 A1 | 2/2003 | Hyodoh et al. | |
| 2003/0055495 A1 | 3/2003 | Pease et al. | |
| 2003/0069635 A1 | 4/2003 | Cartledge et al. | |
| 2003/0109924 A1 | 6/2003 | Cribier | |
| 2003/0125795 A1 | 7/2003 | Pavcnik et al. | |
| 2003/0125805 A1 | 7/2003 | Johnson et al. | |
| 2003/0130729 A1 | 7/2003 | Paniagua et al. | |
| 2003/0149475 A1 | 8/2003 | Hyodoh et al. | |
| 2003/0149476 A1 | 8/2003 | Damm et al. | |
| 2003/0149478 A1 | 8/2003 | Figulla et al. | |
| 2003/0153974 A1 | 8/2003 | Spenser et al. | |
| 2003/0181850 A1 | 9/2003 | Diamond et al. | |
| 2003/0199913 A1 | 10/2003 | Dubrul et al. | |
| 2003/0199963 A1 | 10/2003 | Tower et al. | |
| 2003/0199972 A1 | 10/2003 | Zadno-Aziz et al. | |
| 2003/0212452 A1 | 11/2003 | Zadno-Aziz et al. | |
| 2003/0212454 A1 | 11/2003 | Scott et al. | |
| 2004/0034411 A1 | 2/2004 | Quijano et al. | |
| 2004/0039436 A1 | 2/2004 | Spenser et al. | |
| 2004/0049224 A1 | 3/2004 | Buehlmann et al. | |
| 2004/0049262 A1 | 3/2004 | Obermiller et al. | |
| 2004/0049266 A1 | 3/2004 | Anduiza et al. | |
| 2004/0082904 A1 | 4/2004 | Houde et al. | |
| 2004/0088045 A1 | 5/2004 | Cox | |
| 2004/0098112 A1 | 5/2004 | DiMatteo et al. | |
| 2004/0111096 A1 | 6/2004 | Tu et al. | |
| 2004/0116951 A1 | 6/2004 | Rosengart | |
| 2004/0117004 A1 | 6/2004 | Osborne et al. | |
| 2004/0122468 A1 | 6/2004 | Yodfat et al. | |
| 2004/0127979 A1 | 7/2004 | Wilson | |
| 2004/0138742 A1 | 7/2004 | Myers et al. | |
| 2004/0138743 A1 | 7/2004 | Myers et al. | |
| 2004/0186563 A1 | 9/2004 | Lobbi | |
| 2004/0215339 A1 | 10/2004 | Drasler et al. | |
| 2005/0085841 A1 | 4/2005 | Eversull et al. | |
| 2005/0085842 A1 | 4/2005 | Eversull et al. | |
| 2005/0085843 A1 | 4/2005 | Opolski et al. | |
| 2005/0085890 A1 | 4/2005 | Rasumssen et al. | |
| 2005/0096692 A1 | 5/2005 | Linder et al. | |
| 2005/0096734 A1 | 5/2005 | Majercak et al. | |
| 2005/0096735 A1 | 5/2005 | Hojeibane et al. | |
| 2005/0096738 A1 | 5/2005 | Cali et al. | |
| 2005/0209065 A1 | 9/2005 | Schlosser | |
| 2005/0251251 A1 | 11/2005 | Cribier | |
| 2006/0052867 A1 | 3/2006 | Revuelta et al. | |
| 2006/0247762 A1* | 11/2006 | Acosta et al. | 623/1.24 |
| 2007/0185565 A1* | 8/2007 | Schwammenthal et al. | 623/1.24 |

FOREIGN PATENT DOCUMENTS

| | | |
|---|---|---|
| EP | 0937439 B1 | 9/2003 |
| EP | 1340473 | 9/2003 |
| EP | 1356793 | 10/2003 |
| EP | 0810913 | 6/2004 |
| EP | 1229864 B1 | 4/2005 |
| FR | 2 826 863 | 1/2003 |
| WO | WO 93/15693 | 8/1993 |
| WO | WO 95/04556 | 2/1995 |
| WO | WO 95/29640 | 11/1995 |
| WO | WO 96/14032 | 5/1996 |
| WO | WO 98/36790 | 8/1998 |
| WO | WO 00/09059 | 2/2000 |
| WO | WO 00/44308 | 8/2000 |
| WO | WO 00/44313 | 8/2000 |
| WO | WO 00/67661 | 11/2000 |
| WO | WO 01/05331 | 1/2001 |
| WO | WO 01/35870 | 5/2001 |
| WO | WO 01/64137 | 9/2001 |
| WO | WO 02/36048 | 5/2002 |
| WO | WO 02/100297 | 12/2002 |
| WO | WO 03/003943 | 1/2003 |
| WO | WO 03/003949 | 1/2003 |
| WO | WO 03/011195 | 2/2003 |
| WO | WO 03/015851 | 2/2003 |
| WO | WO 2004/019811 | 3/2004 |
| WO | WO 2004/023980 | 3/2004 |
| WO | WO 2004/041126 | 5/2004 |
| WO | WO 2004/047681 | 6/2004 |
| WO | WO 2005/013860 | 2/2005 |

OTHER PUBLICATIONS

P. Bonhoeffer, MD et al., "Percutaneous Replacement of Pulmonary Valve in a Right-Ventricle to Pulmonary-Artery Prosthetic Conduit with Valve Dysfunction," pp. 1403-1405; Oct. 2000.

Y. Boudjemline, MD, et al., "Steps Towards Percutaneous Aortic Valve Replacement," pp. 775-778; Feb. 2002.

P. Bonhoeffer, MD, et al., "Percutaneous Insertion of the Pulmonary Valve," Journal of the American College of Cardiology, vol. 39, No. 10, pp. 1664-1669; Feb. 2002.

A Cribier, MD, et al., "Percutaneous Transcatheter Implantation of an Aortic Valve Prosthesis for Calcific Aortic Stenosis—First Human Description," pp. 3006-3008; Dec. 2002.

A. Cribier, MD, et al.; "Early Experience with Percutaneous Transcatheter Implantation of Heart Valve Prosthesis for the Treatment of End-Stage Inoperable Patients with Calcific Aortic Stenosis," Journal of the American College of Cardiology, vol. 43, No. 4, pp. 698-703; Nov. 2003.

Y. Boudjemline, MD. et al., "Percutaneous Pulmonary Valve Replacement in a Large Right Ventricular Outflow Tract," Journal of the American College of Cardiology, vol. 43, No. 6; pp. 1082-1087; Mar. 2004.

Andersen, H.R. et al, "Tran luminal implantation of artificial heart valves. Description of a new expandable aortic valve and initial results with implantation by catheter technique in closed chest pigs." Euro. Heart J. (1992) 13:704-708.

Bonhoeffer, "Percutaneous insertion of the pulmonary valve," Journal of American College of Cardiology Foundation, (2002) 39(0):1664-1669.

Iliopoulos, et al., "Repeat replacement of aortic valve bioprosthesis," Ann. Thorac Surg. (1995), 59:1217-1219.

* cited by examiner

VALVED CONDUIT DESIGNED FOR SUBSEQUENT CATHETER DELIVERED VALVE THERAPY

TECHNICAL FIELD

This invention relates generally to medical devices for treating cardiac valve abnormalities, and particularly to a pulmonary valve replacement system and method of employing the same.

BACKGROUND OF THE INVENTION

Heart valves, such as the mitral, tricuspid, aortic and pulmonary valves, are sometimes damaged by disease or by aging, resulting in problems with the proper functioning of the valve. Heart valve problems generally take one of two forms: stenosis, in which a valve does not open completely or the opening is too small, resulting in restricted blood flow; or insufficiency, in which blood leaks backward across a valve when it should be closed.

The pulmonary valve regulates blood flow between the right ventricle and the pulmonary artery, controlling blood flow between the heart and the lungs. Pulmonary valve stenosis is frequently due to a narrowing of the pulmonary valve or the pulmonary artery distal to the valve. This narrowing causes the right side of the heart to exert more pressure to provide sufficient flow to the lungs. Over time, the right ventricle enlarges, which leads to congestive heart failure (CHF). In severe cases, the CHF results in clinical symptoms including shortness of breath, fatigue, chest pain, fainting, heart murmur, and in babies, poor weight gain. Pulmonary valve stenosis most commonly results from a congenital defect, and is present at birth, but is also associated with rheumatic fever, endocarditis, and other conditions that cause damage to or scarring of the pulmonary valve. Valve replacement may be required in severe cases to restore cardiac function.

Previously, valve repair or replacement required open-heart surgery with its attendant risks, expense, and extended recovery time. Open-heart surgery also requires cardiopulmonary bypass with risk of thrombosis, stroke, and infarction. More recently, flexible valve prostheses and various delivery devices have been developed so that replacement valves can be implanted transvenously using minimally invasive techniques. As a consequence, replacement of the pulmonary valve has become a treatment option for pulmonary valve stenosis.

The most severe consequences of pulmonary valve stenosis occur in infants and young children when the condition results from a congenital defect. Frequently, the pulmonary valve must be replaced with a prosthetic valve when the child is young, usually less than five years of age. However, as the child grows, the valve can become too small to accommodate the blood flow to the lungs that is needed to meet the increasing energy demands of the growing child, and it may then need to be replaced with a larger valve. Alternatively, in a patient of any age, the implanted valve may fail to function properly due to calcium buildup and have to be replaced. In either case, repeated surgical or transvenous procedures are required.

To address the need for pulmonary valve replacement, various implantable pulmonary valve prostheses, delivery devices and surgical techniques have been developed and are presently in use. One such prosthesis is a bioprosthetic, valved conduit comprising a glutaraldehyde treated bovine jugular vein containing a natural, trileaflet venous valve, and sinus. A similar device is composed of a porcine aortic valve sutured into the center of a woven fabric conduit. A common conduit used in valve replacement procedures is a homograft, which is a vessel harvested from a cadaver. Valve replacement using either of these devices requires thoracotomy and cardiopulmonary bypass.

When the valve in the prostheses must be replaced, for the reasons described above or other reasons, an additional surgery is required. Because many patients undergo their first procedure at a very young age, they often undergo numerous procedures by the time they reach adulthood. These surgical replacement procedures are physically and emotionally taxing, and a number of patients choose to forgo further procedures after they are old enough to make their own medical decisions.

Recently, implantable stented valves have been developed that can be delivered transvenously using a catheter-based delivery system. These stented valves comprise a collapsible valve attached to the interior of a tubular frame or stent. The valve can be any of the valve prostheses described above, or it can be any other suitable valve. In the case of valves in harvested vessels, the vessel can be of sufficient length to extend beyond both sides of the valve such that it extends to both ends of the valve support stent.

The stented valves can also comprise a tubular portion or "stent graft" that can be attached to the interior or exterior of the stent to provide a generally tubular internal passage for the flow of blood when the leaflets are open. The graft can be separate from the valve and it can be made from any suitable biocompatible material including, but not limited to, fabric, a homograft, porcine vessels, bovine vessels, and equine vessels.

The stent portion of the device can be reduced in diameter, mounted on a catheter, and advanced through the circulatory system of the patient. The stent portion can be either self-expanding or balloon expandable. In either case, the stented valve can be positioned at the delivery site, where the stent portion is expanded against the wall of a previously implanted prostheses or a native vessel to hold the valve firmly in place.

One embodiment of a stented valve is disclosed in U.S. Pat. No. 5,957,949 titled "Percutaneous Placement Valve Stent" to Leonhardt, et al, the contents of which are incorporated herein by reference.

One drawback of using a stented valve is that the stents are often difficult to properly position within a conduit resulting in a misplaced valve. Additionally, stented valves may migrate along the conduit after implantation due to forces applied by the blood flow through the vessel.

It would be desirable, therefore, to provide an implantable pulmonary valve that can readily be positioned and prevented from migrating along a conduit, and would overcome the limitations and disadvantages inherent in the devices described above.

SUMMARY OF THE INVENTION

It is an object of the present invention to provide a vascular valve replacement system having at least a delivery catheter and a replacement valve device disposed on the delivery catheter. The replacement valve device includes a prosthetic valve connected to a valve support region of an expandable support structure. The valve support region includes a plurality of protective struts disposed between a first stent region and a second stent region.

The system and the prosthetic valve will be described herein as being used for replacing a pulmonary valve. The pulmonary valve is also known to those having skill in the art as the "pulmonic valve" and as used herein, those terms shall be considered to mean the same thing.

Thus, one aspect of the present invention provides a system for treating a vascular condition. The system comprises a conduit including an inner wall and at least one locking member positioned on or within the inner wall of the conduit. The system also includes a stented valve positioned in contact with the locking member.

Another aspect of the invention provides another embodiment of a system for treating a vascular condition. The system comprises a conduit operably attached to a vessel, the conduit including an inner wall and at least one locking member attached to the inner wall. The system further includes a delivery catheter and a stented valve removably disposed at a distal end of the delivery catheter for delivery to a treatment site within the conduit. The stent valve includes at least one mating portion complementary to the at least one locking member.

Another aspect of the invention provides a method for treating a vascular condition. The method comprises inserting a conduit with a stented valve into a target region of a vessel, positioning a contact portion of the stented valve against a locking portion of the conduit and preventing migration of the stented valve within the conduit based on the positioning.

The present invention is illustrated by the accompanying drawings of various embodiments and the detailed description given below. The drawings should not be taken to limit the invention to the specific embodiments, but are for explanation and understanding. The detailed description and drawings are merely illustrative of the invention rather than limiting, the scope of the invention being defined by the appended claims and equivalents thereof The drawings are not to scale. The foregoing aspects and other attendant advantages of the present invention will become more readily appreciated by the detailed description taken in conjunction with the accompanying drawings.

DESCRIPTION OF THE PRESENTLY PREFERRED EMBODIMENTS

The invention will now be described by reference to the drawings wherein like numbers refer to like structures.

Figure 1:
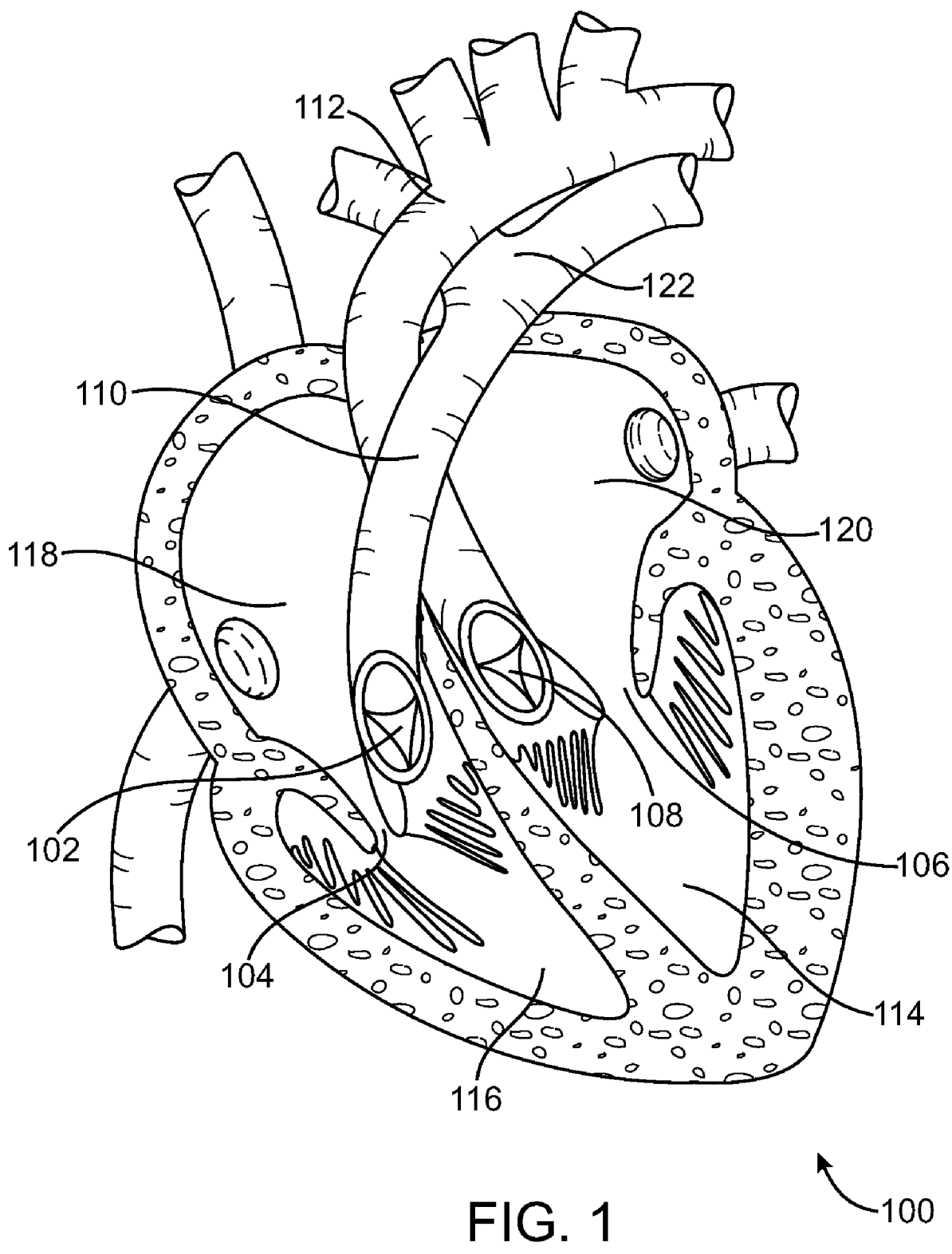
FIG. 1 is a schematic interior view of a human heart showing the functioning of the four heart valves.

Referring to the drawings, FIG. 1 is a schematic representation of the interior of human heart 100. Human heart 100 includes four valves that work in synchrony to control the flow of blood through the heart. Tricuspid valve 104, situated between right atrium 118 and right ventricle 116, and mitral valve 106, between left atrium 120 and left ventricle 114 facilitate filling of ventricles 116 and 114 on the right and left sides, respectively, of heart 100. Aortic valve 108 is situated at the junction between aorta 112 and left ventricle 114 and facilitates blood flow from heart 100, through aorta 112 to the peripheral circulation.

Pulmonary valve 102 is situated at the junction of right ventricle 116 and pulmonary artery 110 and facilitates blood flow from heart 100 through the pulmonary artery 110 to the lungs for oxygenation. The four valves work by opening and closing in harmony with each other. During diastole, tricuspid valve 104 and mitral valve 106 open and allow blood flow into ventricles 114 and 116, and the pulmonic valve and aortic valve are closed. During systole, shown in FIG. 1, aortic valve 108 and pulmonary valve 102 open and allow blood flow from left ventricle 114, and right ventricle 116 into aorta 112 and pulmonary 110, respectively.

The right ventricular outflow tract is the segment of pulmonary artery 110 that includes pulmonary valve 102 and extends to branch point 122, where pulmonary artery 110 forms left and right branches that carry blood to the left and right lungs respectively. A defective pulmonary valve or other abnormalities of the pulmonary artery that impede blood flow from the heart to the lungs sometimes require surgical repair or replacement of the right ventricular outflow tract with prosthetic conduit 202, as shown in FIG. 2A-C.

Such conduits comprise tubular structures of biocompatible materials, with a hemocompatible interior surface. Examples of appropriate biocompatible materials include polytetrafluoroethylene (PTFE), woven polyester fibers such as Dacron® fibers (E.I. Du Pont De Nemours & Co., Inc.), and bovine vein crosslinked with glutaraldehyde. One common conduit is a homograft, which is a vessel harvested from a cadaver and treated for implantation into a recipient's body. These conduits may contain a valve at a fixed position within the interior lumen of the conduit that functions as a replacement pulmonary valve.

One such conduit 202 comprises a bovine jugular vein with a trileaflet venous valve preserved in buffered glutaraldehyde. Other valves are made of xeno-pericardial tissue and are attached to the wall of the lumen of the conduit. Still other valves may be made at least partially from some synthetic material. The conduits may also include materials having a high X-ray attenuation coefficient (radiopaque materials) that are woven into or otherwise attached to the conduit, so that it can be easily located and identified.

Figure 2A:
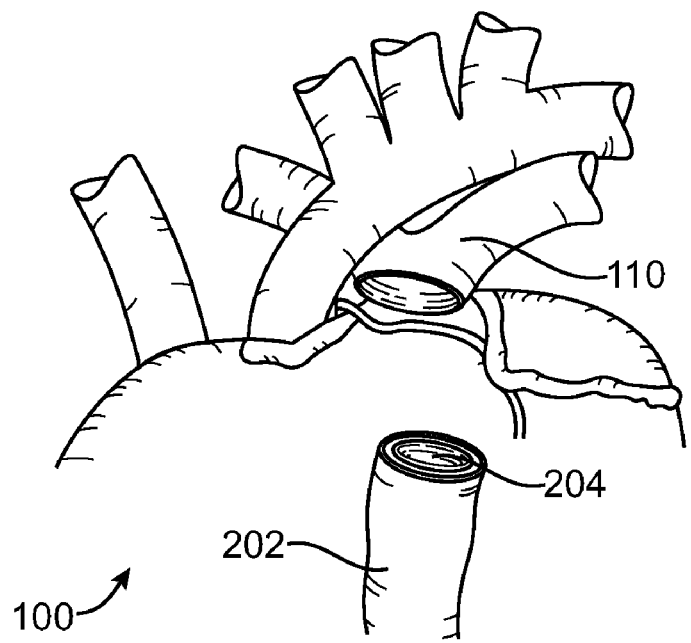
FIG. 2A is a schematic view showing the placement of a pulmonary conduit, as is known in the prior art.
Figure 2B:
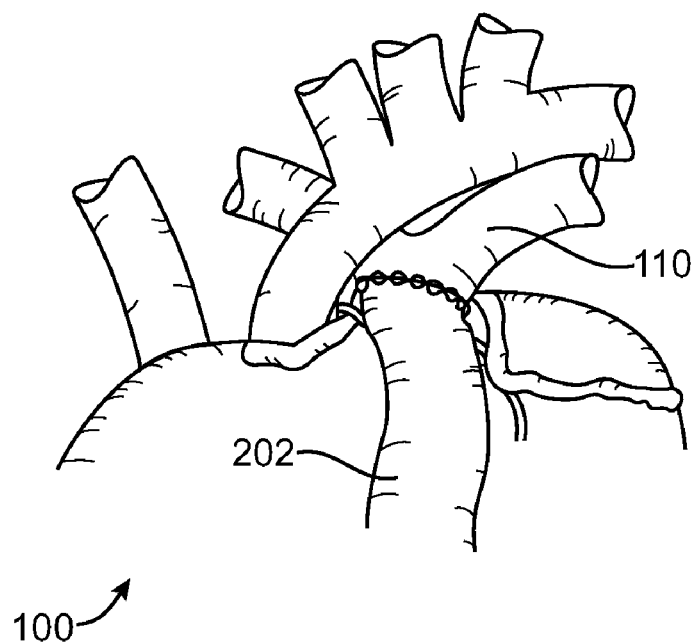
FIG. 2B is a schematic view showing attachment of a pulmonary conduit to the pulmonary artery, as is known in the prior art.
Figure 2C:
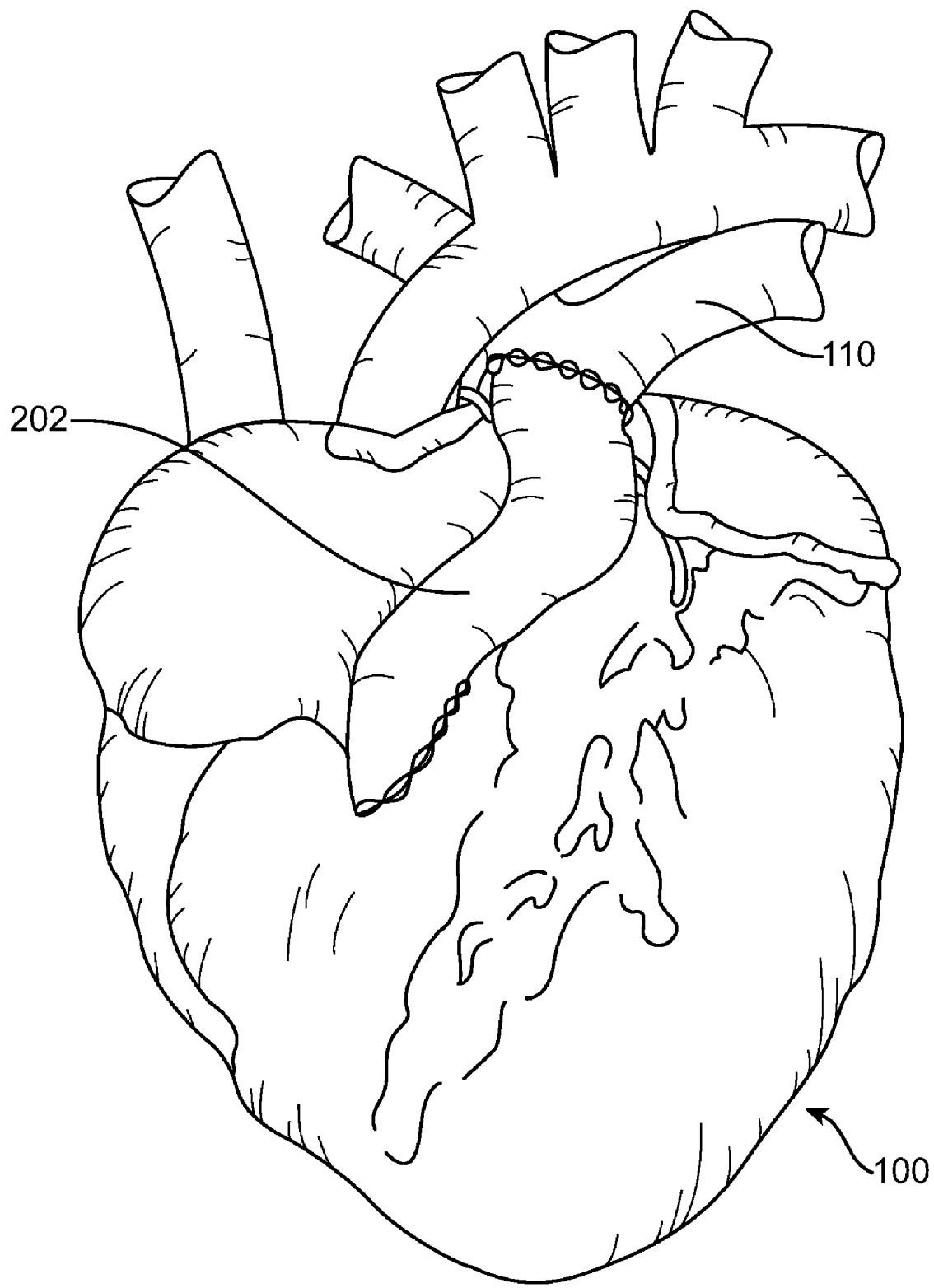
FIG. 2C is a schematic view showing attachment of a pulmonary conduit to the heart, as is known in the prior art.

As shown in FIGS. 2A and 2B, conduit 202, which houses valve 204 within its inner lumen, is installed within a patient by sewing the distal end of conduit 202 to pulmonary artery 110, and, as shown in FIG. 2C, attaching the proximal end of conduit 202 to heart 100 so that the lumen of conduit 202 connects to right ventricle 116.

Over time, implanted prosthetic conduits and valves are frequently subject to calcification, causing the affected conduit or valve to lose flexibility, become misshapen, and lose the ability to function effectively. Additional problems are encountered when prosthetic valves are implanted in young children. As the child grows, the valve will ultimately be too small to handle the increased volume of blood flowing from the heart to the lungs. In either case, the valve needs to be replaced.

The current invention discloses devices and methods for percutaneous catheter based placement of stented valves for regulating blood flow through a pulmonary artery. In a preferred embodiment, the valves are attached to an expandable support structure and they are placed in a valved conduit that is been attached to the pulmonary artery, and that is in fluid communication with the right ventricle of a heart. The support structure can be expanded such that any pre-existing valve in the conduit is not disturbed, or it can be expanded such that any pre-existing valve is pinned between the support structure and the interior wall of the conduit.

The delivery catheter carrying the stented valve is passed through the venous system and into a patient's right ventricle. This may be accomplished by inserting the delivery catheter into either the jugular vein or the subclavian vein and passing it through superior vena cava into right atrium. The catheter is then passed through the tricuspid valve, into right ventricle, and out of the ventricle into the conduit. Alternatively, the catheter may be inserted into the femoral vein and passed through the common iliac vein and the inferior vena cava into the right atrium, then through the tricuspid valve, into the right ventricle and out into the conduit. The catheters used for the procedures described herein may include radiopaque markers as are known in the art, and the procedure may be visualized using fluoroscopy, echocardiography, ultrasound, or other suitable means of visualization.

Figure 3A:
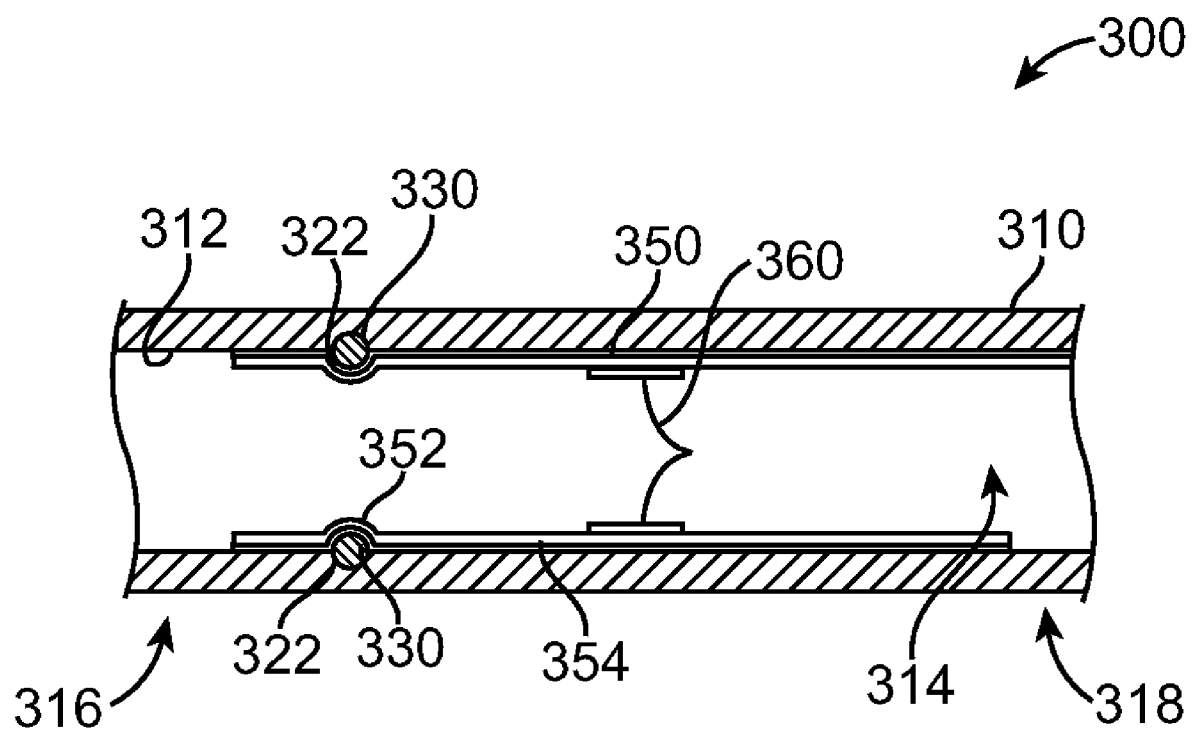
FIG. 3A is a schematic view of one embodiment of a prosthetic valve device situated in a conduit, in accordance with the present invention.
Figure 4:
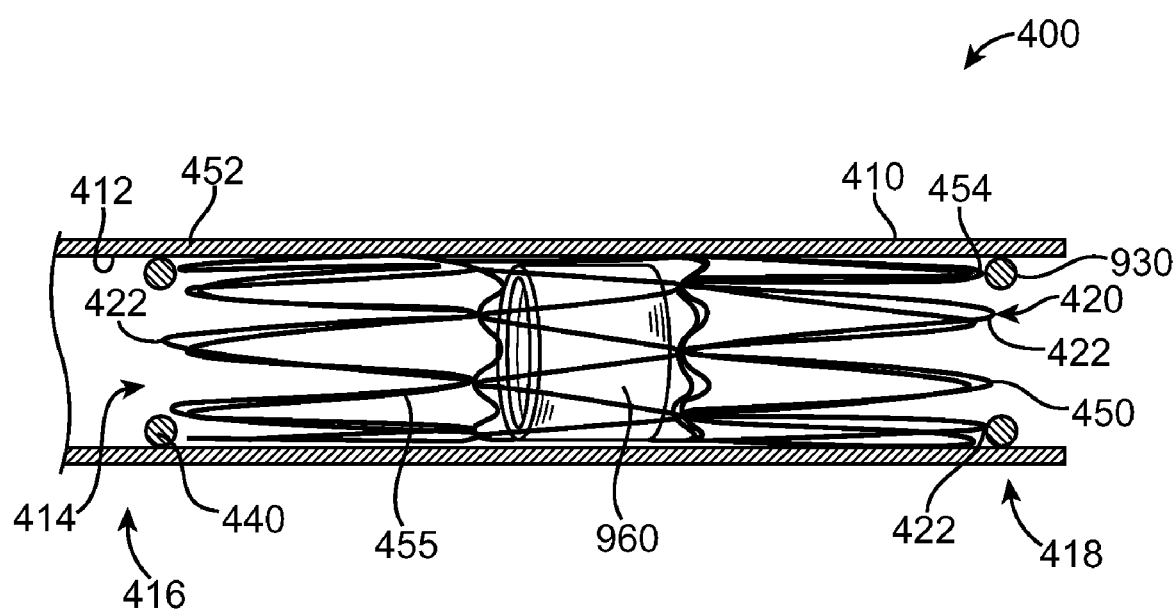
FIG. 4 is a schematic view of another embodiment of a prosthetic valve device situated in a conduit, in accordance with the present invention.
Figure 5A:
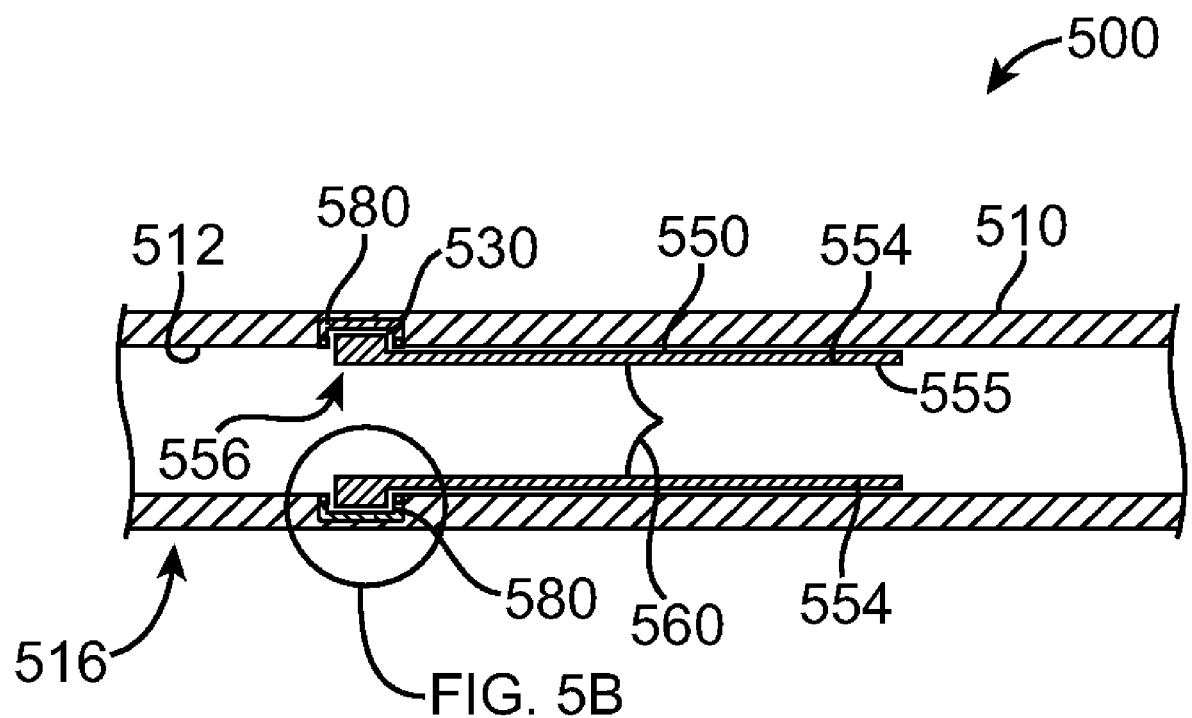
FIG. 5A is a schematic view of another embodiment of a prosthetic valve device situated in a conduit, in accordance with the present invention.

FIG. 3A illustrates a cross section of one embodiment of a system 300 for treating a vascular condition within heart 100 illustrated in FIG. 1. System 300 illustrated in FIG. 3A, as well as those illustrated in FIGS. 4 and 5A, are described herein with reference to a bioprosthetic conduit for replacing a portion of a pulmonary artery. Those with skill in the art will recognize that the invention may be adapted to other vessels of a body that require a replacement valve.

System 300 is illustrated in an expanded configuration as it would appear in place within a bioprosthetic conduit. System 300 comprises a bioprosthetic conduit 310, locking member 330 and a stented valve 350. Conduit 310 comprises an elongate tubular structure that includes an inner wall 312 that defines a lumen 314. Lumen 314 allows fluid communication between the right ventricle and the pulmonary artery. Conduit 310 includes a first end 316 for attaching to ventricle 110 and a second end 318 for attaching to pulmonary artery 122.

Locking member 330 is disposed on or within inner wall 312 of conduit 310. In one embodiment, locking member 330 is disposed adjacent end 316. Locking member 330 is securely attached to conduit 310. In one embodiment, locking member 330 is sutured to the conduit adjacent an inner wall 312. In another embodiment, locking member 330 is incorporated into the woven material of the conduit.

Locking member 330 is composed of a biocompatible material. The biocompatible material may be, for example, a biocompatible metallic material, a polymeric material or a combination thereof. Examples of biocompatible metallic materials include, but are not limited to nitinol, stainless steel, a cobalt-based alloy, and a nickel cobalt super alloy. Examples of biocompatible polymeric materials include, but are not limited to, amides, polyimides, polyolefins, polyesters, urethanes, thermoplastics, thermoset plastics, and blends, laminates or copolymers thereof. In one embodiment, locking member 330 comprises stainless steel.

Figure 7:
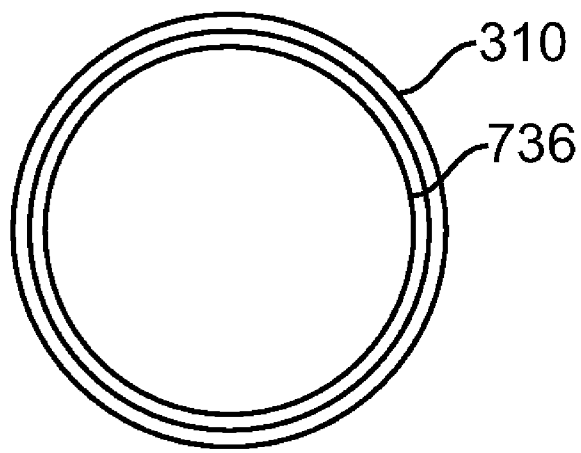
FIG. 7 is a schematic view of one embodiment of a locking member that may be utilized in the device of FIG. 3A, made in accordance with the present invention.
Figure 8:
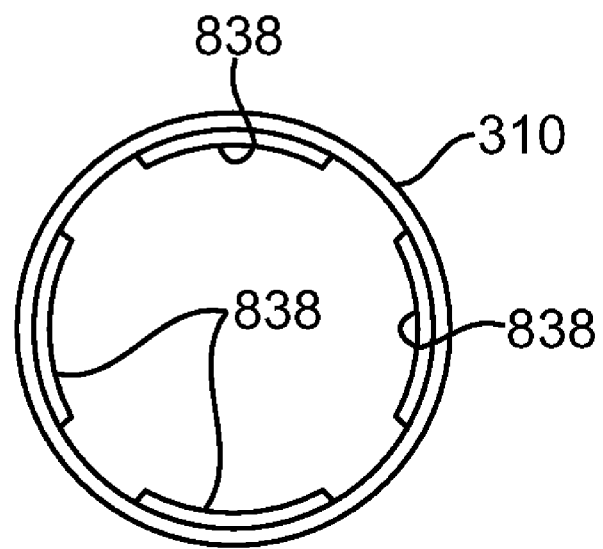
FIG. 8 is a schematic view of another embodiment of a locking member that may be utilized in the device of FIG. 3A, made in accordance with the present invention.

In one embodiment illustrated in FIG. 7, the locking member comprises a ring member 736. In another embodiment, locking member 330 comprises a semicircular member. In yet another embodiment, the locking member comprises at least one arched member. In another embodiment illustrated in FIG. 8, the locking member 330 comprises a plurality of spaced apart arched members 838.

Figure 3B:
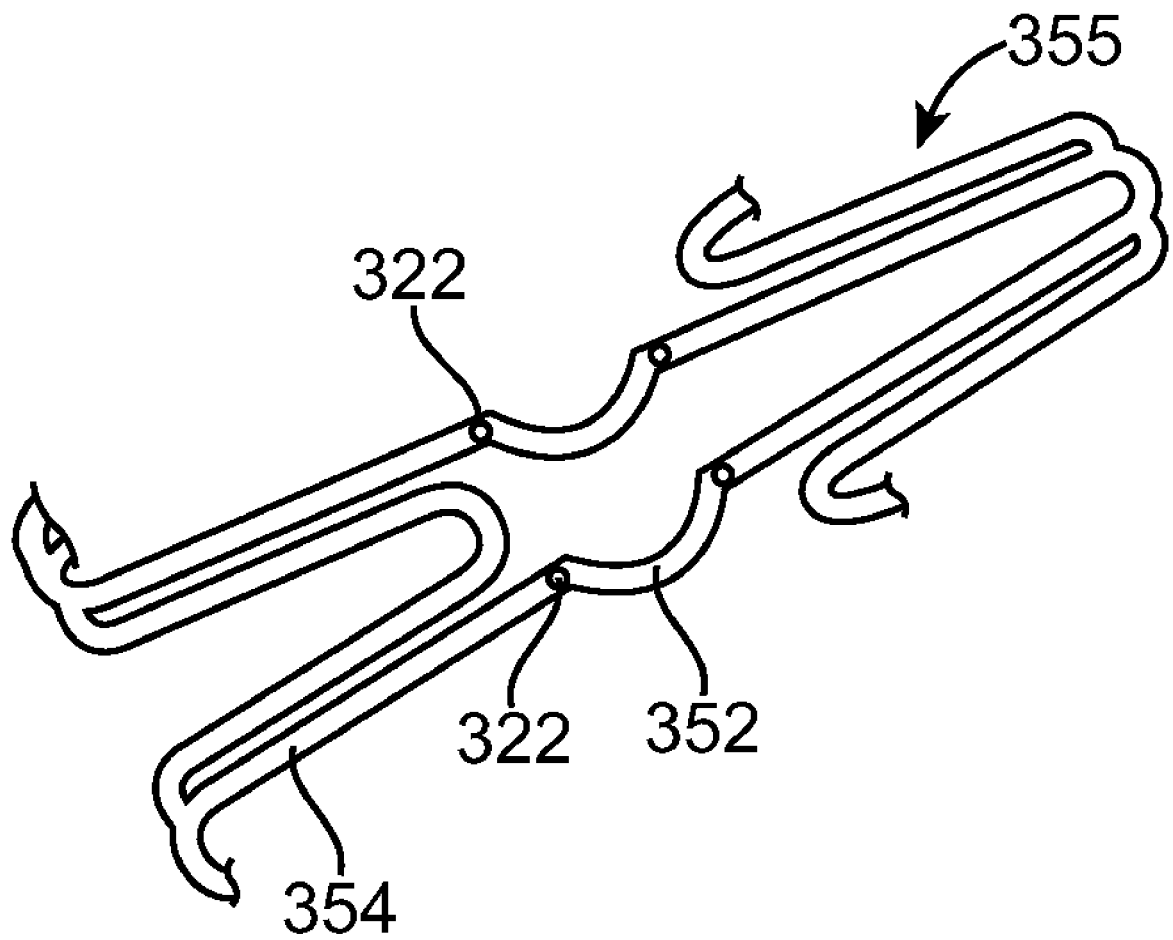
FIG. 3B is a schematic view showing a detailed portion of the device illustrated in FIG. 3A.

Stented valve 350 comprises a stent framework 355 and a prosthetic valve 360. In one embodiment of the invention, stent framework 355 is a stent made of a flexible, biocompatible material that has "shape memory." Examples of suitable materials include, but are not limited to, a nitinol alloy, a stainless steel, and a cobalt-based alloy such as MP35N® alloy. In one embodiment, prosthetic valve 360 comprises a bovine jugular vein with a trileaflet venous valve preserved in buffered glutaraldehyde. In other embodiments, prosthetic valve 360 comprises a valve made of synthetic materials and attached to the stent framework 355. Prosthetic valve 360 is operably attached to stent framework by any means known in the art. In one embodiment, prosthetic valve 360 is attached to stent framework 355 by suturing. Referring to FIG. 3B, stent framework comprises a plurality of strut members 354. Stent framework includes at least one receiving portion 352 disposed on at least one strut 354. Receiving portion 352 is complementary to locking member 330 and is configured to mate with locking member 330 when in the expanded configuration. In one embodiment, receiving portion 352 comprises an arch that is complementary to a ring-shaped locking member 330 having a circular cross section. Locking member 330 and receiving portion 352 are sized to reduce migration of the stent along the conduit after implantation of the stented valve 350. In one embodiment, the complementary fit between locking member 330 and receiving portion 352 comprises a snap fit. In another embodiment, locking member 330 is sized to create an obstruction such that movement of the stented valve is reduced or eliminated by contact with receiving portion 352.

In one embodiment, system 300 also includes materials having a high X-ray attenuation coefficient (radiopaque materials) so that the stented valve 350 can be easily located and positioned within conduit 310 adjacent the locking member 330. Referring to FIGS. 3A and 3B, system 300 includes radiopaque markers 322. In one embodiment, a plurality of radiopaque markers 322 are disposed on struts 354 adjacent receiving portion 352. In one embodiment, a radiopaque marker 322 is disposed on each side of receiving portion 352 in a spaced apart configuration. In this embodiment, locking member 330 includes radiopaque material disposed on and/or within the locking member. For example, in one embodiment locking member 330 includes a plurality of radiopaque markers disposed on the surface of a ring shaped member. Radiopaque markers may include radiopaque metals such as, for example, gold and platinum. In another embodiment, a polymeric locking member 330 includes a radiopaque component added during the manufacture of the polymeric material. Examples of suitable radiopaque material that can be added to the polymeric material include, but are not limited to, barium sulfate and bismuth sub-carbonate.

FIG. 4 illustrates a partial cross section of another embodiment of a system 400 for treating a vascular condition within heart 100 illustrated in FIG. 1.

System 400 is illustrated in an expanded configuration as it would appear in place within a bioprosthetic conduit. System 400 comprises a bioprosthetic conduit 410, locking members 430, 440 and a stented valve 450. Conduit 410 comprises an elongate tubular structure that includes an inner wall 412 that defines a lumen 414. Lumen 414 allows fluid communication between the right ventricle and the pulmonary artery. Conduit 410 includes a first end 416 for attaching to ventricle 116 and a second end 418 for attaching to pulmonary artery 110.

Stented valve 450 comprises a stent framework 455 and a prosthetic valve 460. In one embodiment of the invention, stent framework 455 is a stent made of a flexible, biocompatible material that has "shape memory", such as nitinol. In one embodiment, prosthetic valve 460 comprises a bovine jugular vein with a trileaflet venous valve preserved in buffered glutaraldehyde. In other embodiments, prosthetic valve 460 comprises a valve made of synthetic materials and attached to the stent framework 455. Prosthetic valve 460 is operably attached to stent framework by any means known in the art. In one embodiment, prosthetic valve 460 is attached to stent framework 455 by suturing. One embodiment of a stented valve suitable for use in the present invention is disclosed in U.S. Pat. No. 5,957,949 titled "Percutaneous Placement Valve Stent" to Leonhardt, et al., which is assigned to the same assignee as the present application. The contents of the '949 Patent are hereby incorporated by reference.

Locking members 430, 440 are disposed adjacent inner wall 412 of conduit 410 in a spaced apart configuration. In one embodiment, locking members 430 and 440 are spaced apart a predetermined distance. In one embodiment, the predetermined distance corresponds to the length of a stented valve 460 when the stented valve is in an expanded configuration disposed within the conduit. In one embodiment, the distance between locking members 430, 440 is substantially the same as the length of a stented valve. In another embodiment, the distance between locking members 430, 440 is greater than the length of a stented valve. In one embodiment, locking members 430, 440 are positioned within conduit 410 on either side of the conduit valve. Locking members 430, 440 are composed of biocompatible material the same as, or similar to, those described above for locking member 330.

In one embodiment, locking members 430 and 440 comprise a first ring member 430 and a second ring member 440. In another embodiment, locking members 430, 440 comprise semicircular members. In yet another embodiment, each of locking members 430, 440 comprise at least one arched member. In another embodiment, each of locking members 430, 440 comprise a plurality of spaced apart arched members. Locking members 430 and 440 are securely attached to conduit 410. Locking members 430 and 440 are attached to conduit 410 in a manner similar to or the same as locking member 330.

Locking members 430 and 440 are sized to prevent the migration of stented valve 450 within conduit 410 after implantation of the stented valve 450. In one embodiment, a first end 452 of stented valve 450 abuts locking member 440 and a second end 454 abuts locking member 430 when stented valve is in the expanded configuration within conduit 410. In another embodiment, first end 452 of stented valve 450 is adjacent locking member 440 and a second end 454 is adjacent locking member 430 when stented valve is in the expanded configuration within conduit 410.

In one embodiment, system 400 also includes materials having a high X-ray attenuation coefficient (radiopaque materials) so that the stented valve 450 can be easily located and positioned within conduit 410 adjacent the locking member 430, 440. In one embodiment, a plurality of radiopaque markers 422 are disposed on stent framework 455 at or adjacent strut apex 422. Locking members 430, 440 may also include radiopaque markers the same as or similar to that described above for locking member 330. For example, in one embodiment locking member 430, 440 includes a plurality of radiopaque markers disposed on the surface of a ring shaped member. Radiopaque markers may include radiopaque metals such as, for example, gold and platinum. In another embodiment, a polymeric locking member 430, 440 includes a radiopaque component added during the manufacture of the polymeric material. Examples of suitable radiopaque material that can be added to the polymeric material include, but are not limited to, barium sulfate and bismuth sub-carbonate.

Figure 5B:
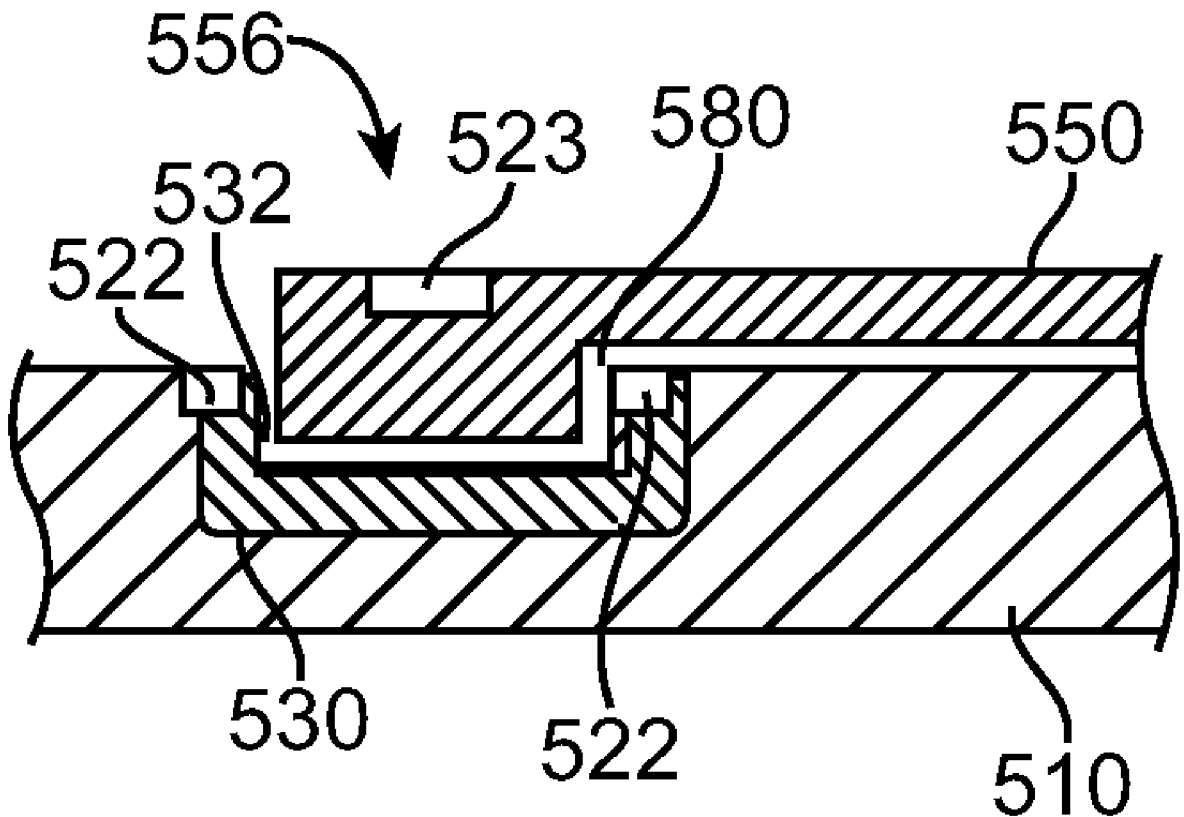
FIG. 5B is a schematic view showing a detailed portion of the device illustrated in FIG. 5A.

FIGS. 5A and 5B illustrate a cross section of one embodiment of a system 500 for treating a vascular condition within heart 100 illustrated in FIG. 1. System 500 is illustrated in an expanded configuration as it would appear in place within a bioprosthetic conduit. System 500 comprises a bioprosthetic conduit 510, locking member 530 and a stented valve 550. Conduit 510 comprises an elongate tubular structure that includes an inner wall 512 that defines a lumen 514. Lumen 514 allows fluid communication between the right ventricle and the pulmonary artery. Conduit 510 includes a first end 516 for attaching to ventricle 116 and a second end 518 for attaching to pulmonary artery 110.

Locking member 530 is disposed adjacent inner wall 512 of conduit 510. In one embodiment, locking member 530 is disposed adjacent end 516. Locking member 530 is composed of biocompatible material the same as, or similar to, those described above for locking member 330.

In one embodiment, locking member 530 comprises a ring member. In another embodiment, locking member 530 comprises a semicircular member. In yet another embodiment, locking member 530 comprises at least one arched member. In another embodiment, locking member 530 comprises a plurality of spaced apart arched members. Locking member 530 is securely attached to conduit 510. In one embodiment, locking member 530 is sutured to the conduit adjacent an inner wall 512. In another embodiment, locking member 530 is incorporated into the woven material of a conduit composed of, for example, polyester fibers. Referring to FIG. 5B, locking member 530 includes a locking channel 532. In one embodiment, locking channel 532 comprises a groove along the inner circumference of locking member 530.

Stented valve 550 comprises a stent framework 555 and a prosthetic valve 560. In one embodiment of the invention, stent framework 555 is a stent made of a flexible, biocompatible material that has "shape memory", such as nitinol. In one embodiment, prosthetic valve 560 comprises a bovine jugular vein with a trileaflet venous valve preserved in buffered glutaraldehyde. In other embodiments, prosthetic valve 560 comprises a valve made of synthetic materials and attached to the stent framework 555. Prosthetic valve 560 is operably attached to stent framework by any means known in the art. In one embodiment, prosthetic valve 560 is attached to stent framework 555 by suturing.

Referring to FIGS. 5A and 5B, stent framework 555 comprises a plurality of strut members 554. In one embodiment, at least one strut member includes a mating portion 580 disposed at a proximal end 556 of strut member 554. Mating portion 580 extends radially from strut member 554. Mating portion 580 is complementary in shape to locking channel 532 and is configured to mate with locking channel 532 when the stented valve is in the expanded configuration. In one embodiment, the complementary fit between locking channel 532 and mating portion 580 comprises a snap fit. In another embodiment, the proximal ends 556 of the strut members 554 having a mating portion include a spring bias to position and retain the mating portion 580 within locking channel 532.

In one embodiment, system 500 also includes materials having a high X-ray attenuation coefficient (radiopaque materials) so that the stented valve 550 can be easily located and positioned within conduit 510 adjacent the locking member 530. Referring to FIG. 5B, mating portion 580 of strut member 554 includes a radiopaque marker 523. Locking member 530 includes radiopaque markers and/or material on the periphery of locking channel 532. Radiopaque marker and/or material may be the same as or similar to that described above for locking member 330. Radiopaque markers may include radiopaque metals such as, for example, gold and platinum. In another embodiment, a polymeric locking member 530 includes a radiopaque component added during the manufacture of the polymeric material. Examples of suitable radiopaque material that can be added to the polymeric material include, but are not limited to, barium sulfate and bismuth sub-carbonate.

Figure 6:
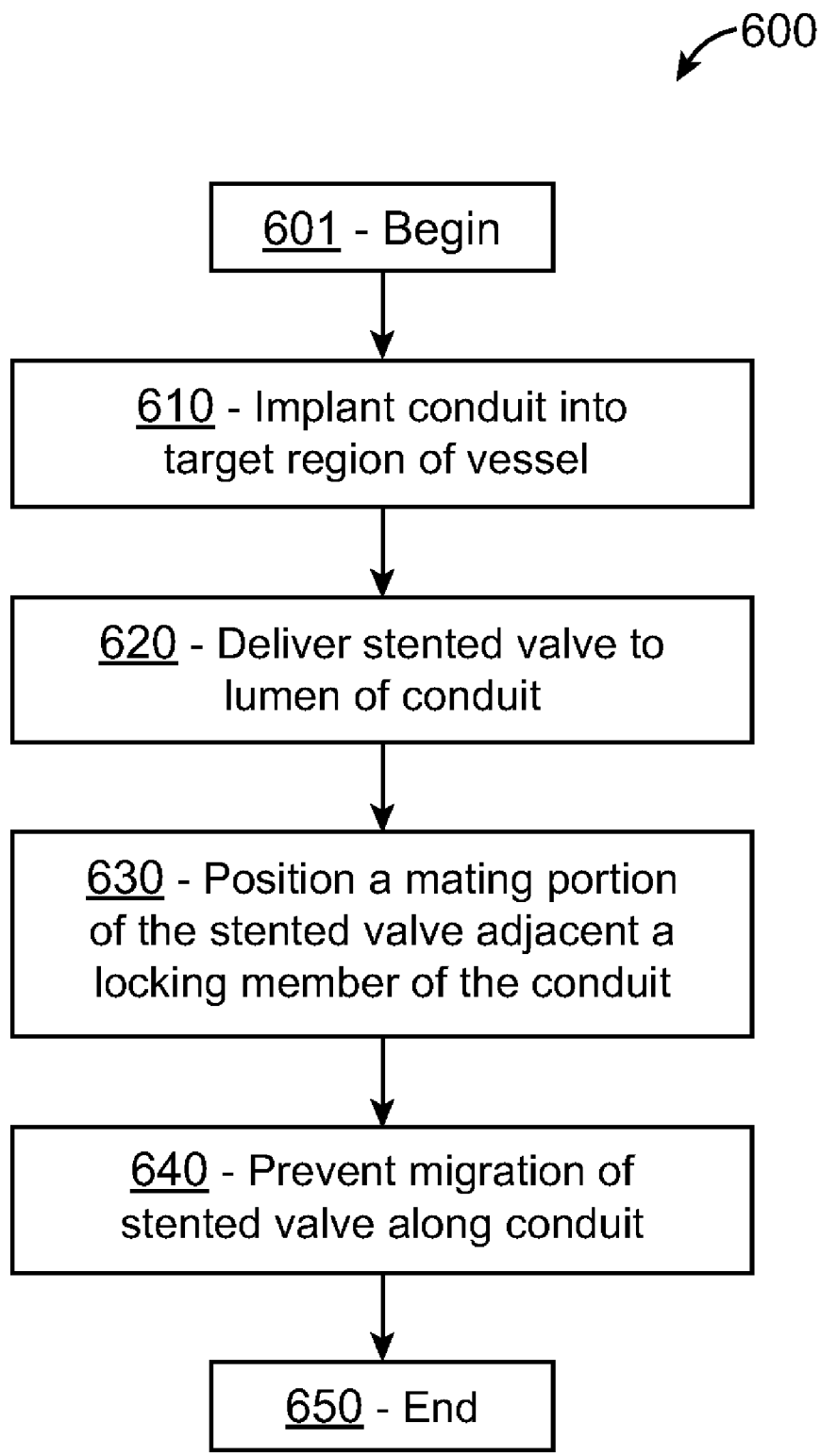
FIG. 6 illustrates one embodiment of a method of treating a vascular condition in accordance with the present invention.

FIG. 6 is a flowchart illustrating method 600 for treating right ventricular outflow tract abnormalities by replacing a pulmonary valve, in accordance with the present invention. Method 600 begins at step 601.

At step 610, a bioprosthetic conduit including at least one locking member is implanted into a target region of a vessel. In one embodiment, the bioprosthetic conduit includes a first locking member and a second locking member, the locking members in a spaced apart configuration.

Next, a stented valve is delivered into a target site within a lumen of the bioprosthetic conduit, at step 620. In one embodiment, the stented valve is delivered percutaneously via a delivery catheter as are known in the art. In one embodiment, the target site within the conduit lumen comprises that portion of the lumen between the spaced apart locking members.

At step 630, the stented valve is expanded to position a mating portion of the stented valve into contact with at least a portion of the locking member. In one embodiment, the stented valve is positioned between the first and second locking members in an abutting configuration. In one embodiment, the stented valve is expanded into position using a balloon. In another embodiment, the stented valve comprises a self-expanding stent that expands radially when released from the delivery catheter. In one embodiment, the stented valve is positioned by aligning a radiopaque marker located on a portion of the stented valve with another radiopaque marker located on the locking member.

At step 640, the stented valve is prevented from migrating along the bioprosthetic conduit based on positioning the mating portion into contact with the locking member. Method 600 ends at 650.

While the invention has been described with reference to particular embodiments, it will be understood by one skilled in the art that variations and modifications may be made in form and detail without departing from the spirit and scope of the invention.

What is claimed is:

1. A system for treating a vascular condition, comprising:
   a conduit including an inner wall;
   at least one locking member positioned on or within the inner wall of the conduit, wherein the locking member comprises a ring; and
   an expandable stent having a prosthetic valve disposed therein, wherein the stent can be positioned in contact with the at least one locking member.

2. The system of claim 1 wherein the stent includes a complementary receiving portion to mate with the locking member.

3. The system of claim 1 wherein the at least one locking member includes a first locking member and a second locking member spaced apart from the first locking member.

4. The system of claim 3 wherein a first end of the stent contacts with a portion of the first locking member and a second end of the stented valve contacts with a portion of the second locking member when the stent is in an expanded configuration.

5. A system for treating a vascular condition, comprising:
   a conduit including an inner wall;
   at least one locking member positioned on or within the inner wall of the conduit, wherein the at least one locking member comprises a ring member, the ring member including a locking channel disposed along an inner circumference of the ring member and
   an expandable stent having a prosthetic valve disposed therein, wherein the stent can be positioned in contact with the at least one locking member.

6. The system of claim 5 wherein the stent comprises at least one strut member, the at least one strut member including a mating portion complementary to the locking channel and wherein the mating portion contacts the locking channel in a locking configuration when the stented valve is in an expanded configuration.

7. A system for treating a vascular condition, comprising:
   a conduit including an inner wall;
   at least one locking member positioned on or within the inner wall of the conduit, wherein the at least one locking member comprises a semicircular locking member; and
   an expandable stent having a prosthetic valve disposed therein, wherein the stent can be positioned in contact with the at least one locking member.

8. The system of claim 7 wherein the semicircular locking member includes a locking channel disposed along an inner circumference of the semicircular locking member.

9. The system of claim 8 wherein the stent comprises at least one strut member, the at least one strut member including a mating portion complementary to the locking channel and wherein the mating portion contacts the locking channel in a locking configuration when the stent is in an expanded configuration.

10. A system for treating a vascular condition, comprising:
    a conduit operably attached to a vessel, the conduit including an inner wall and at least one locking member attached to the inner wall, wherein the at least one locking member comprises a ring member disposed at a proximal end of the conduit;
    a delivery catheter; and
    a stented valve having a prosthetic valve disposed in a stent with a plurality of strut members, wherein at least one of the strut members includes a mating portion complementary to the at least one locking member,
    wherein the stented valve is removably disposed at a distal end of the delivery catheter for delivery to a treatment site.

11. The system of claim 10 wherein the mating portion comprises an arched member for receiving the ring member.

12. A system for treating a vascular condition, comprising:
    a conduit operably attached to a vessel, the conduit including an inner wall and at least one locking member attached to the inner wall, wherein the at least one locking member comprises a ring member, the ring member including a locking channel disposed along an inner circumference of the ring member
    a delivery catheter; and a stented valve having a prosthetic valve disposed in a stent with a plurality of strut members, wherein at least one of the strut members includes a mating portion complementary to the at least one locking member, wherein the stented valve is removably disposed at a distal end of the delivery catheter for delivery to a treatment site.

13. The system of claim 12 wherein the stented valve comprises at least one strut member, the at least one strut member including a mating portion complementary to the locking channel and wherein the mating portion contacts the locking channel in a locking configuration when the stented valve is in an expanded configuration.

14. A system for treating a vascular condition, comprising:

a conduit operably attached to a vessel, the conduit including an inner wall and at least one locking member attached to the inner wall;

a delivery catheter;

a stented valve having a prosthetic valve disposed in a stent with a plurality of strut members, wherein at least one of the strut members includes a mating portion complementary to the at least one locking member;

a first radiopaque marker disposed on a portion of the locking member; and a second radiopaque marker disposed on a portion of the mating member wherein the stented valve is removably disposed at a distal end of the delivery catheter for delivery to a treatment site.

15. A method for treating a vascular condition, the method comprising:

inserting a conduit with a locking member into a target region of a vascular system;

positioning a contact portion of a stented valve against the locking member of the conduit; and preventing migration of the stented valve within the conduit based on the positioning.

16. The method of claim 15 further comprising:

aligning a first radiopaque marker disposed on or adjacent the contact portion of the stented valve with a second radiopaque portion located on the locking member.

* * * * *

UNITED STATES PATENT AND TRADEMARK OFFICE
CERTIFICATE OF CORRECTION

PATENT NO. : 7,625,403 B2
APPLICATION NO. : 11/278646
DATED : December 1, 2009
INVENTOR(S) : Mike Krivoruchko It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 609 days.

Signed and Sealed this

Twenty-sixth Day of October, 2010

David J. Kappos
*Director of the United States Patent and Trademark Office*